US008586053B2

(12) United States Patent
Thomas

(10) Patent No.: US 8,586,053 B2
(45) Date of Patent: *Nov. 19, 2013

(54) COMPOSITION AND USE OF PHYTO-PERCOLATE FOR TREATMENT OF DISEASE

(75) Inventor: Tiffany Thomas, Phoenix, AZ (US)

(73) Assignee: Health Enhancement Products, Inc., Bloomfield Hills, MI (US)

( * ) Notice: Subject to any disclaimer, the term of this patent is extended or adjusted under 35 U.S.C. 154(b) by 761 days.

This patent is subject to a terminal disclaimer.

(21) Appl. No.: 12/067,735

(22) PCT Filed: Apr. 20, 2006

(86) PCT No.: PCT/US2006/015302
§ 371 (c)(1),
(2), (4) Date: Oct. 3, 2008

(87) PCT Pub. No.: WO2006/113925
PCT Pub. Date: Oct. 26, 2006

(65) Prior Publication Data
US 2009/0036372 A1 Feb. 5, 2009

Related U.S. Application Data

(60) Provisional application No. 60/719,025, filed on Sep. 21, 2005, provisional application No. 60/741,774, filed on Dec. 2, 2005.

(51) Int. Cl.
*A61K 36/02* (2006.01)

(52) U.S. Cl.
USPC .................................................. 424/195.17

(58) Field of Classification Search
None
See application file for complete search history.

(56) References Cited

U.S. PATENT DOCUMENTS

| 4,822,612 | A | 4/1989 | Shinpo | |
|---|---|---|---|---|
| 6,461,607 | B1 | 10/2002 | Farmer | |
| 6,551,596 | B2 | 4/2003 | Kralovec | |
| 6,733,751 | B2 | 5/2004 | Farmer | |
| 7,807,622 | B2 * | 10/2010 | Thomas et al. | 514/4.8 |
| 2002/0009479 | A1 | 1/2002 | Vardi et al. | |
| 2002/0119164 | A1 * | 8/2002 | Uchiyama et al. | 424/195.15 |
| 2003/0152587 | A1 | 8/2003 | Kralovec | |
| 2005/0114920 | A1 * | 5/2005 | Yusibov et al. | 800/280 |
| 2007/0010480 | A1 | 1/2007 | Rusing et al. | |

FOREIGN PATENT DOCUMENTS

| JP | 409040523 A * | 2/1997 |
|---|---|---|
| WO | WO 03028749 A1 * | 4/2003 |
| WO | WO2005/112987 | 1/2005 |
| WO | 2005112987 | 12/2005 |
| WO | WO2006/113925 | 10/2006 |
| WO | WO2007/065024 | 6/2007 |

OTHER PUBLICATIONS

International Search Report for Patent Application No. PCT/US2010/056862 dated Jul. 29, 2011.
International Search Report for Patent Application No. PCT/US2011/025713 dated Jun. 21, 2011.
Article entitled "Arteriosclerosis, Thrombosis, and Vascular Biology: Regulation of Plasma High-Density Lipoprotein Levels by the ABCA1 Transporter and the Emerging Role of High-Density Lipoprotein in the Treatment of Cardiovascular Disease," by H. Bryan Brewer, Jr. Alan T. Remaley, Edward B. Neufeld, Federica Basso and Charles Joyce. Published by the American Heart Association, originally published online Aug. 19, 2004.
Australian Examiner's Report for Patent Application No. PCT/US2006/046320 dated Aug. 25, 2011.
Office Action dated Sep. 9, 2011 for U.S. Appl. No. 12/947,684.
Notice of Allowance dated Aug. 27, 2010 for U.S. Appl. No. 11/606,676.
06758513.3-2403 PCT/US2006015302 European search report dated Sep. 24, 2009.
Communication pursuant to Article 94(e) EPC dated Nov. 20, 2009 for International Patent Application No. 06758513.3-2403.
Article entitled "Lipids in Health and Disease: The effects of ProAlgaZyme novel algae infusion on metabolic syndrome and markers of cardiovascular health," by Julius Oben, Ebangha Enonchong, Dieudonne Kuate, Dora Mbanya, Tiffany C. Thomas, DeWall J Hildreth, Thomas D Ingolia and Micheal S. Tempesta. Published in BioMed Central, Sep. 5, 2007, p. 1-9.
Press Release entitled "Western Glory Hole Inc. Enters Definitive Agreement with Health Enhancement Products Inc." dated Oct. 30, 2003, Business Wire.
Office Action for International Patent Application No. 06838974.1 dated Feb. 23, 2010.
Abstract entitled "A water-soluble antitumor glycoprotein from *Chlorella vulgaris*," by Noda K, Ohno N, Tanaka K, Kamiya N, Okuda M, Yadomae T, Nornoto K, Shoyama Y. Department of Pharmacognosy, Faculty of Pharmaceutical Sciences, Kyushu University, Fukuoka, Japan, dated Oct. 1996. PubMed.
Written Opinion of the international Searching Authority dated Dec. 6, 2009 for International Patent Application No. PCT/US05/13375.
International Preliminary Report on Patentability dated Oct. 25, 2006 for International Patent Application No. PCT/US05/013375.
Written Opinion of the International Searching Authority dated Mar. 22, 2007 for International Patent Application No. PCT/US06/15302.
International Preliminary Report on Patentability dated Oct. 23, 2007 for International Patent Application No. PCT/US2006/015302.
International Search Report dated Jun. 4, 2008 for International Patent Application No. PCT/US06/46320.
Final Office Action dated Nov. 3, 2008 for U.S. Appl. No. 11/587,266.

(Continued)

*Primary Examiner* — Terry A McKelvey
*Assistant Examiner* — Randall Winston
(74) *Attorney, Agent, or Firm* — Snell & Wilmer L.L.P.

(57) ABSTRACT

This invention relates generally to a method of preparation of a phyto-percolate that is derived from fresh water mixture including algae. The invention further relates to the use of the phyto-percolate in a variety of disease states. The phyto-percolate is believed to contain an activity that induces the reduction of soluble and insoluble fibrin. Further, the phyto-percolate is believed to reduce oxidative stress in the body.

14 Claims, 3 Drawing Sheets

(56) References Cited

OTHER PUBLICATIONS

Nonfinal Office Action dated Feb. 4, 2008 for U.S. Appl. No. 11/587,266.
Spirulina. (2010). MedlinePlus. U.S. National Library of Medicine and the National Institutes of Health. Retrieved Apr. 14, 2010 from http://www.nlm.nih.gove/medlineplus/druginfo/natural/patient-spirulina.html as accessed Apr. 14, 2010.
BioSuperfood—Algae/Spirulina for People. (2010). Optimum Choices. Retrieved Apr. 14, 2010 from http://www.optimumchoices.com/spirulina.htm as accessed Apr. 14, 2010.
Kim et al. Purification and characterization of a fibrinolytic enzyme produced from *Bacillus* sp. strain CK 11-4 screened from Chungkook-Jang. Appl. Environ. Microbiology, Jul. 1996, vol. 62, No. 7, pp. 2482-2488, p. 2482, In 4: abstract.
The Magic of Bio-Algae Concentrates. (2003) Michael Kiriac.
Nonfinal Office Action dated Feb. 4, 2008 for U.S. Appl. No. 11/606,676.
Final Office Action dated Nov. 14, 2008 for U.S. Appl. No. 11/606,676.
Non-Final Office Action dated Oct. 8, 2009 for U.S. Appl. No. 11/606,676.
Final Office Action dated May 29, 2009 for U.S. Appl. No. 11/606,676.
International Search Report dated Oct. 17, 2007 for International Patent Application No. PCT/US06/46320.
International Search Report dated Mar. 22, 2007 for International Patent Application No. PCT/US06/15302.
International Search Report dated Dec. 6, 2005 for International Patent Application No. PCT/US05/13375.
EPO Communication re: European Patent Application No. 10830908.9 dated Mar. 7, 2012.
EPO Communication re: European Patent Application No. 06758513.3 dated Mar. 22, 2012.
Office Action dated May 21, 2012 for U.S. Appl. No. 12/947,684.
Scientific Paper Pub. Jun. 2012 in the Journal of Nutrition and Dietary Supplements by Smiti Gupta and group at WSU.
Australian Patent Examination Report dated Sep. 7, 2012.
U.S. Appl. No. 12/897,574, filed Oct. 4, 2010, Composition and Use of Phyto-Percolate for Treatment of Disease.
U.S. Appl. No. 12/947,684, filed Nov. 16, 2010, Composition and Method for Affecting Cytokines and NF-kB.
U.S. Appl. No. 13/841,739, filed Mar. 15, 2013, Composition and Method for Affecting Cytokines and NF-kB.
Office Action dated Dec. 20, 2012 in U.S. Appl. No. 12/947,684.
Sarkar et al, "Using Chemopreventive Agents to Enhance the Efficacy of Cancer Therapy," Cancer Res. 2006; 66: (7), Apr. 1, 2006, pp. 3347-3350.
Office Action dated Jun. 24, 2013 in U.S. Appl. No. 12/897,574.
Office Action dated May 24, 2013 in Canadian Patent Application No. 2,631,773.
Office Action dated Aug. 7, 2012 in Japanese Patent Application No. 2008543545.
"Research Indicates ProAlgaZyme may Decrease Risk of Stroke or Heart Attack," Jan. 20, 2004, retrieved online: http://www.supplementquality.com/efficacy/ProAlgaZyme.html.

* cited by examiner

COMPOSITION AND USE OF PHYTO-PERCOLATE FOR TREATMENT OF DISEASE

CROSS-REFERENCE TO RELATED APPLICATIONS

This application is the National Stage Application of International Application No. PCT/US06/15302, filed Apr. 20, 2006, which claims priority to U.S. Provisional Application Ser. No. 60/741,774 filed Dec. 2, 2005 and U.S. Provisional Application Ser. No. 60/719,025 filed Sep. 21, 2005, which are incorporated herein by reference in their entirety.

FIELD OF INVENTION

This invention relates generally to methods and compositions for treating and preventing human diseases, disorders, and conditions using a preparation of a phyto-percolate isolated from a complex mixture of fresh water algae and other microorganisms.

BACKGROUND OF INVENTION

Enzymes have a very important use within biochemical cycles in the human body. The majority of acute and chronic diseases create an inflammatory process that results in the destruction of surrounding tissue. This tissue debris becomes toxic and further hinders the processes of detoxification, elimination and defense by way of free radical oxidation. Proteolytic enzymes are responsible for the body's detoxification processes. As humans age and chronic disease processes progress, a deficiency of the proteolytic enzymes that carry out the body's waste detoxification processes may be experienced. This enzymatic deficiency aids in the production of a chronic hyper-inflammatory state, and the disease process becomes much more complex.

Enzymes are the catalysts that control and direct all metabolic processes. Without adequate enzymes in the body, chaos reigns and the immune system and other metabolic processes become less efficient, making tissue repair slow and poorly replicated. Proteolytic enzymes, or proteases, are enzymes capable of breaking down proteins by cleaving peptide bonds. They are produced and utilized by every living organism on Earth for protection, nutrient breakdown and assimilation, and waste removal. Many degenerative diseases stem from proteolytic enzyme deficiencies, leading to the inadequate removal of carcinogenic wastes from the body.

It is believed that the immune system, which helps protect us from diseases including cancer, cardiovascular disease, and other immune deficient or deregulated disorders, can become ineffective because of advanced disease state or age. Immune deficiency caused by disease state or advancing age can impair benefits received from the use of therapeutic drugs that may be taken for the treatment of these various disorders. Therapeutic drugs may lose their effectiveness in a compromised immune system as a disease state progresses due to metabolic dysfunction or poor therapeutic drug assimilation.

With advancing age, humans experience an increasing accumulation of damage resulting from environmental influences that are believed to be toxic. An observed effect associated with aging is a less accurate tissue repair process, including DNA mutation repair. Because of these alterations, pathogens (e.g., microbes), and environmental toxins (e.g., radiation and chemical compounds) increasingly produce deleterious effects.

Human genes, which are made up of double-strands of DNA, are the directors of tissue repair. It is believed that through advancing age and contact with the surrounding destructive elements, the expression of such DNA may become less and less accurate because of replication errors and mutations, thus creating very different functional end products of repair when compared to a younger individual.

Impaired immune protection and regulation, it is believed, allows an increasing amount of toxic environmental components to invade the cells of our bodies. These toxic components express destructive patterns of oxidation by way of free radical activity, thus rendering important metabolic processes to function inadequately. Because of biochemical cellular destruction, dead, fractionated cellular components are created, adding to the toxic manifestations. White cells, which are an important part of the immune system, congregate at the sites of tissue destruction in an effort to slow the process down. A chemical reaction that takes place at the site causes inflammation that further increases the destructive pattern. This pattern of tissue destruction, secondary to foreign antigen invasion and the associated white cell activity, can create an ongoing autoimmune hyperactive inflammatory state and an increasing amount of toxic tissue destruction and debris. Because of the increased inefficiency of tissue repair and the ever presence of surrounding environmental influences, human metabolic processes become less and less efficient with age.

The inner lining of the blood vessels, particularly the arteries, can be affected by this destructive pattern. Because many environmental contaminants are introduced into human bodies through the intestinal tract and lungs, they spread through the body by way of the vasculature, thus coming first in contact with the inner lining of the blood vessels. This ongoing contact in the inner lining of the arteries with toxic free radicals results in the destructive oxidative process. This maintains an ongoing inflammatory state that includes cell break down and scar tissue formation in the form of sclerotic plaques. These plaques are made up of fibrous tissue, cholesterol, calcium deposits and necrotic tissue (broken down cellular components). Increasing arterial restriction and blood thickening due to pathological fibrin diminishes blood flow and alters oxygen and nutrient distribution to vital organs. This gradually increasing cellular starvation affects the functions of the brain, heart, kidneys, muscles, joints and other vital systems.

It is believed that accelerated DNA mutations and errors in replication, increased oxidation, inflammation, dysregulated white cell activity, and tissue destruction are the results of a gradual progression of contact with environmental forces, including pathogenic microbials, in conjunction with genetic disposition. The amount of contact depends on lifestyle and individual health care. Some illnesses either originate from excessive free radical oxidation destruction at the body's cellular level, or cause a great increase in free radical oxidation destruction. Therefore, when the body's own metabolic and healing processes are unable to cope with the excess of toxic waste products, a cycle of ongoing inflammation and disease is created that interferes with the body's normal immune activity and tissue repair. Tissue destruction also activates the body's coagulation, or blood-clotting, mechanism, generating a barrage of intra-vascular thrombi, or blood clots, and blood-thickening fibrin, that can precipitate strokes, heart attacks, pulmonary emboli, kidney damage, and phlebitis.

Oxidative free radical activity becomes rampant because of the action of the involving white cells attempting to control the initial cause of the destruction. The resulting pathological agents secondary to this influence of white cell activity create an ongoing destructive pattern upon local surrounding tissue, the endothelial cells that line the vascular bed, and the epithelial cells lining the intestinal tract. Not only is there destructive activity upon the above-mentioned tissues but also there is oxidative breakdown or pathological activation of the coagulation factors. This includes pathologically activated fibrinogen to produce a soluble fibrin that, unlike insoluble fibrin, which is an important component of the normal blood-clotting mechanism, cannot be cross-linked and is pathological, or harmful to the body. This soluble fibrin not only negatively influences general capillary circulation but also kidney filtration, oxygen exchange within the alveoli of the lungs, and oxygenation of brain tissue. It not only thickens the blood, but is in itself an oxidative free radical, and contributes to the degenerative oxidation process.

Causes of the expressed symptomatology from the production of soluble fibrin include gram-negative bacteria, *mycoplasma* and *Candida albicans*, which may flourish in the immune-compromised environment created by excess wastes and fibrin, and is related to the cellular destruction and by-products of ongoing free radical activity. Fibrinolytic activity, or the process of breaking down fibrin, along with the eradication of the foreign pathological agents by other therapeutic interventions and a reduction in oxidative activity, can lead to increasingly effective immune system and white cell activity, and will greatly accelerate the healing process.

Most cancer processes liberate hydrogen peroxide, which acts as a free radical oxidative agent. In addition to hydrogen peroxide, the effects of cancer growth and chemotherapy produce excess soluble fibrin products as a response to these abnormal and destructive processes. The fibrin is produced as part of the body's natural reaction to tissue damage, which also occurs normally at the site of a superficial wound for clotting purposes. However, at the site of cancer growth, fibrin sometimes coats cancer cells, thereby insulating them from destruction by the body's immune system. These coagulation mechanisms, stimulated by the oxidative damage associated with chronic illness, the damaging effects of chemotherapy, and the nature of abnormal cancer growth, all lead to further damage. Chronic illnesses such as cancer produce an acceleration of disseminated intravascular coagulation, causing not only a build-up of soluble fibrin but also of small intravascular thrombi that may obstruct circulation in a vascular bed. The use of a fibrinolytic agent, along with any other therapeutic regime, will increase immune regulation and the effectiveness of white cell activity, improve capillary circulation and nutrient flow to the body's organs, aid in eliminating toxins, and enhance the benefits of other therapeutic agents. In addition, fibrinolytic agents will reduce the amount of free radical soluble fibrin that accelerates degenerative oxidation, and can increase the body's immune effectiveness in combating cancer growth.

In vivo laboratory monitoring of disease processes has supported the observations that improved cellular function and efficiency come with less oxidative, free radical activity, improved cellular nutrition, enhanced immune activity and white cell function and improved oxygenation.

SUMMARY OF THE INVENTION

In one aspect, the invention provides a method for treating or preventing a disorder in an animal (e.g., human, dog, cat, horse, cow, chicken, etc.) by administering to the animal a therapeutically effective amount of phyto-percolate or derivative thereof.

The phyto-percolate of this invention is a complex aqueous mixture of micro- and macronutrient, including macromolecules (e.g., proteins, glycoproteins, lipids, polysaccharides, etc.). It is these micro- and macronutrients that are the phyto-percolate derivatives. One of the most prevalent classes of phyto-percolate derivatives is protein. In particularly useful embodiments of the invention, the phyto-percolate is a protein or mixture of proteins that have an apparent molecular weight of about 21.0 kDa and 67.5 kDa. Also included are homomultimers and heteromultimers such as homo- and hetero-dimers, homo- and hetero-trimers, homo- and hetero-tetramers, etc. In another embodiment, the phyto-percolate derivative has fibrinolytic activity or causes increased fibrinolytic activity in the animal or the cells exposed to the phyto-percolate or derivative thereof. The phyto-percolate derivative may be isolated from the phyto-percolate or it may be produced by any appropriate method known in the art. Suitable methods for producing the phyto-percolate derivative include, for example, recombinantly or naturally expressing the derivative (e.g., protein) using a microorganism, synthetically producing a derivative (i.e., chemical (cell-free) synthesis), extracting the derivative(s) from the culture media or cellular contents of one or more of the species present in ATCC Deposit #PTA-5863, or administering derivative together with live or processed cells or cell components. For embodiments in which the phyto-percolate derivative is produced using a microorganism, any suitable naturally occurring or recombinant microorganism may be used. In useful embodiments, the phyto-percolate derivative is produced using a naturally-occurring species present in ATCC Deposit #PTA-5863, or a recombinant variant thereof.

In particular embodiments, a useful dosage of the phyto-percolate is between about 1 and about 20 ounces per day for a human or animal, preferably about 1 to about 4 ounces per day for a human. In other useful embodiments, the administered phyto-percolate contains between about 1 ppm and about 150 ppm of at least one phyto-percolate derivative. In another useful embodiment, a therapeutically effective amount of more than one phyto-percolate derivatives is administered. Preferably, the human or animal is administered between about <1 mg and 1000 mg of the derivative per day. Suitable methods for administration of the phyto-percolate or phyto-percolate derivative include, for example, oral (e.g., ingestion), sublingual, topical, rectal, bronchial (e.g., as an inhalant, nasal spray, etc), or vaginal administration as well as intravenous, intramuscular, and subcutaneous injection. The phyto-percolate and phyto-percolate derivatives are particularly useful for the treatment of mastitis in cows. Preferably, the phyto-percolate or phyto-percolate derivative is administered directly to the lumen of the udder.

Another aspect of this invention is directed to a method of treating an overweight condition or obesity comprising administering to the animal (e.g., human) a therapeutically effective amount of a phyto-percolate or derivative thereof.

Another aspect of this invention is directed to a method for treating type I and II diabetes comprising administering to the animal (e.g., human) a therapeutically effective amount of a phyto-percolate or derivative thereof.

Another aspect of this invention is directed to a method for treating an inflammatory disorder comprising administering to the animal (e.g., human) a therapeutically effective amount of a phyto-percolate or derivative thereof. It is believed that the phyto-percolate and derivatives have broad spectrum anti-inflammatory properties and therefore may be used to reduce or prevent inflammation in a wide range of diseases, disorders and injuries.

Another aspect of this invention is directed to a method for treating a stomach disorder comprising administering to the animal (e.g., human) a therapeutically effective amount of a phyto-percolate or derivative thereof. Stomach disorders amenable to treatment with the phyto-percolate and/or derivatives thereof include, for example, a stomach ulcer and gastric reflux disease.

In another aspect of this invention, the phyto-percolate or derivatives may be used to alleviate side-effects or increase effectiveness of another primary therapy. For example, the phyto-percolate may be administered to reduce the oxidative stress, chemotherapy-induced nausea, chemotherapy-induced liver damage, appetite suppression, hair loss, fingernail and toenail loss and discoloration that result from anti-AIDS therapy and anti-cancer therapy (e.g., antiretroviral therapy, chemotherapy and radiation therapy).

In another aspect of this invention, the phyto-percolate or derivatives may be used to reduce the recovery time and soreness in animals (e.g., humans and horses) after periods of stress (e.g., exercise, performance, travel). In a related aspect, the phyto-percolate or derivatives are administered in order to restore physical energy, musculoskeletal function, immune function and mental acuity following periods of physical and mental stress.

In another aspect of this invention, the phyto-percolate or derivatives may be used to reduce the recovery time in animals (e.g., humans and horses) after periods of trauma (e.g., injury). In a related aspect, the phyto-percolate or derivatives are administered in order to aid in recovery, tissue repair, pain management, and excessive inflammation following tissue damage.

In another aspect of this invention, the phyto-percolate or derivates may also be administered topically directly to the eye (e.g., in the form of eye drops) to treat lesions or inflammation of the cornea, dry eyes, and similar ocular disorders.

Another aspect of this invention is directed to a method for treating conditions or disorders associated with infectious disease (e.g., viral, bacterial, or fungal infection) comprising administering to the animal (e.g., human) a therapeutically effective amount of a phyto-percolate or derivative thereof. Infectious disease may be the cause of many of the above and below listed diseases such as pneumonia, all viruses, acariosis, acne, adenovirus, AIDS, amebiasis, anthrax, athlete's food, babesiosis, bartonellosis, Bell's palsy, botulism, candidiasis, carbuncles, Chaga's disease, chicken pox, Chlamydia, coccidiomycosis, coronavirus, cryptococcosis, cytomegalovirus, Dengue fever, echovirus, erysipelas, furuncle, gangrene, Guillan-Barre syndrome, hepatitis, impetigo, influenza, leucopenia, Lyme's disease, malaria, martolditis, measles, mumps, mycobacterium, mycosis, parasites, pediculosis, P.I.D. pyodermia, rabies, rubella, salmonella, salpingitis, septicemia, shingles, sinusitis, syphilis, tetanus, Tindi Cruzi and warts.

Another aspect of this invention is directed to a method for treating diseases related to the heart, blood vessels, renal, liver, and endocrine system comprising administering a therapeutically effective amount of a phyto-percolate or derivative thereof.

Another aspect of this invention is directed to a method for treating a vasospasm comprising administering to an animal (e.g., human) a therapeutically effective amount of a phyto-percolate or derivative thereof.

Another aspect of this invention is directed to a method for treating heart failure comprising administering to an animal (e.g., human) a therapeutically effective amount of a phyto-percolate or derivative thereof.

Another aspect of this invention is directed to a method for treating cardiac hypertrophy comprising administering to an animal (e.g., human) a therapeutically effective amount of a phyto-percolate or derivative thereof.

Another aspect of this invention is directed to a method for treating dysregulated blood pressure comprising administering to an animal (e.g., human) a therapeutically effective amount of a phyto-percolate or derivative thereof.

Another aspect of this invention is directed to a method for treating angina comprising administering to an animal (e.g., human) a therapeutically effective amount of a phyto-percolate or derivative thereof.

Another aspect of this invention is directed to a method for treating peripheral vascular disease comprising administering to an animal (e.g., human) a therapeutically effective amount of a phyto-percolate or derivative thereof.

Another aspect of this invention is directed to a method for treating cerebral diseases and diseases related to the central nervous system that are vascular in origin comprising administering to an animal (e.g., human) a therapeutically effective amount of a phyto-percolate or derivative thereof.

Another aspect of this invention is directed to a method for treating neuro-degeneration comprising administering to an animal (e.g., human) a therapeutically effective amount of a phyto-percolate or derivative thereof.

Another aspect of this invention is directed to a method for treating Alzheimer's disease comprising administering to an animal (e.g., human) a therapeutically effective amount of a compound of a phyto-percolate or derivative thereof.

Another aspect of this invention is directed to a method for treating depression and/or anxiety comprising administering to an animal (e.g., human) a therapeutically effective amount of a phyto-percolate or derivative thereof.

Another aspect of this invention is directed to a method for treating addiction and drug-related afflictions including, for example, the abuse of nicotine, cocaine, methamphetamines, opiates and alcohol comprising administering to an animal (e.g., human) a therapeutically effective amount of a phyto-percolate or derivative thereof. In a related aspect, the phyto-percolate or derivatives are administered in order to aid in drug detoxification comprising administering to an animal (e.g., human) a therapeutically effective amount of a phyto-percolate or derivative thereof.

Another aspect of this invention is directed to a method for treating attention deficit disorder and attention deficit hyperactivity disorder comprising administering to an animal (e.g., human) a therapeutically effective amount of a compound of a phyto-percolate or derivative thereof.

Another aspect of this invention is directed to a method for treating sleep disorders comprising administering to an animal (e.g., human) a therapeutically effective amount of a phyto-percolate or derivative thereof.

Another aspect of this invention is directed to a method for treating seasonal affective disorder comprising administering to an animal (e.g., human) a therapeutically effective amount of a phyto-percolate or derivative thereof.

Another aspect of this invention is directed to a method for treating environmental and food allergies comprising administering to an animal (e.g., human) a therapeutically effective amount of a phyto-percolate or derivative thereof.

Another aspect of this invention is directed to a method for treating conditions related to pain or nocioception comprising administering to an animal (e.g., human) a therapeutically effective amount of a phyto-percolate or derivative thereof.

Another aspect of this invention is directed to a method for treating migraine and tension headaches comprising administering to an animal (e.g., human) a therapeutically effective amount of a compound of a phyto-percolate or derivative thereof.

Another aspect of this invention is directed to a method for treating disorders related to disruption of circadian rhythms including jet lag comprising administering to an animal (e.g., human) a therapeutically effective amount of a phyto-percolate or derivative thereof.

Another aspect of this invention is directed to a method for treating bodily oxidative stress and its symptoms associated with travel (e.g. fatigue, lack of physical energy) comprising administering to an animal (e.g., human) a therapeutically effective amount of a phyto-percolate or derivative thereof. In another related aspect, the phyto-percolate or derivatives are administered in order to prevent infectious diseases associated with travel comprising administering to an animal (e.g., human) a therapeutically effective amount of a phyto-percolate or derivative thereof.

Another aspect of this invention is directed to a method for treating diseases related to abnormal gastrointestinal motility, secretion, and/or function comprising administering to an animal (e.g., human) a therapeutically effective amount of a phyto-percolate or derivative thereof.

Another aspect of this invention is directed to a method for treating diarrhea and/or incontinence comprising administering to an animal (e.g., human) a therapeutically effective amount of a phyto-percolate or derivative thereof.

Another aspect of this invention is directed to a method for treating a gastric ulcer comprising administering to an animal (e.g., human) a therapeutically effective amount of a phyto-percolate or derivative thereof.

Another aspect of this invention is directed to a method for treating irritable bowel syndrome comprising administering to an animal (e.g., human) a therapeutically effective amount of a phyto-percolate or derivative thereof.

Another aspect of this invention is directed to a method for treating inflammatory bowel disease comprising administering to an animal (e.g., human) a therapeutically effective amount of a phyto-percolate or derivative thereof.

Another aspect of this invention is directed to a method for treating nausea or vertigo comprising administering to an animal (e.g., human) a therapeutically effective amount of a phyto-percolate or derivative thereof.

Another aspect of this invention is directed to a method for treating sexual dysfunction comprising administering to an animal (e.g., human) a therapeutically effective amount of a phyto-percolate or derivative thereof.

Another aspect of this invention is directed to a method for altering fertility comprising administering to an animal (e.g., human) a therapeutically effective amount of a phyto-percolate or derivative thereof.

Another aspect of this invention is directed to a method for treating conditions or disorders associated with the immune system comprising administering to an animal (e.g., human) a therapeutically effective amount of a phyto-percolate. Immune system deficiency may be the cause of many of the above and below listed diseases such as cancer, emphysema, encephalitis, environmental sensitivity, erysipelas, food poisoning and Reynaud's disease.

Another aspect of this invention is directed to a method for treating conditions or disorders associated with hormonal imbalances comprising administering to an animal (e.g., human) a therapeutically effective amount of a phyto-percolate. Hormonal imbalances may be the cause of many of the above and below listed diseases such as acne, Addison's disease, endometriosis, Grave's disease, osteoporosis, menstrual and menopausal regulation, glucose, and other metabolic regulation. In this regards, the phyto-percolate and derivatives may be used to improve the general health and overall function of metabolic organs like the kidney, liver, and pancreas. It is believed that the phyto-percolate and derivatives improve the efficiency of those organs and increases their metabolic and endocrine functions.

Another aspect of this invention is directed to a method for treating conditions or disorders associated with neurological deficiencies comprising administering to an animal (e.g., human) a therapeutically effective amount of a phyto-percolate. Neurological deficiencies may be the cause of many of the above and below listed diseases such as Lou Gehrig's disease, chronic pain, Huntingdon's Chorea, diabetic neuropathy, multiple sclerosis, Myasthenia Gravis, Parkinson's disease, poliomyelitis, senile dementia, nigrostriatal degeneration, stroke, tardive dyskinesia and tinnitus.

Another aspect of this invention is directed to a method for treating respiratory diseases comprising administering to an animal (e.g., human) a therapeutically effective amount of a phyto-percolate.

Another aspect of this invention is directed to a method for treating asthma comprising administering to an animal (e.g., human) a therapeutically effective amount of a phyto-percolate.

Another aspect of this invention is directed to a method for treating diseases related to abnormal hormone release and utilization or endocrine function comprising administering to an animal (e.g., human) a therapeutically effective amount of a phyto-percolate.

Another aspect of this invention provides a method for treating abnormal insulin release or utilization, including insulin resistance, comprising administering to an animal (e.g., human) a therapeutically effective amount of a compound of a phyto-percolate.

Another aspect of this invention is directed to a method for treating skin lesions, infections, inflammation and other skin disorders comprising administering to an animal (e.g., human) a therapeutically effective amount of a phyto-percolate.

Another aspect of this invention is directed to a method for supporting fetal development during pregnancy comprising administering to an animal (e.g., human) a therapeutically effective amount of a compound of a phyto-percolate.

Another aspect of this invention is directed to a method for treating the deleterious effects of a systemic or local microbial (e.g., bacterial, viral, or fungal) infection comprising administering to an animal (e.g., human) a therapeutically effective amount of a compound of a phyto-percolate. Such treatment improves or normalizes organ structure and/or function.

Another aspect of this invention is directed to a method for supporting musculo-skeletal rehabilitation following trauma or degenerative disease processes comprising administering to an animal (e.g., human) a therapeutically effective amount of a compound of a phyto-percolate.

Another aspect of this invention is directed to a method for aiding in normalizing hyper-coagulant states including those secondary to endothelial destruction, lipid imbalance and dysfunction, oxidation, and mineral imbalance, comprising administering to an animal (e.g., human) a therapeutically effective amount of a compound of a phyto-percolate.

In addition to the "direct" effect of the phyto-percolate of this invention there are diseases/conditions wherein subjects with said diseases/conditions will benefit from the associated weight loss, and metabolic and immune system regulation, such as individuals with insulin resistance with impaired glucose tolerance, Type II Diabetes, hypertension, hyperlipidemia, cardiovascular disease, gall stones, certain cancers, sleep apnea, etc. resulting from use of phyto-percolate.

In a further illustrative embodiment a method of making the inventive phyto-percolate is disclosed. The phyto-percolate is prepared by cultivating a mixture of freshwater algae and bacteria that is augmented by a nutrient blend that is related to the production of phyto-percolate derivatives, forming a fortified algae culture. Added to this fortified algal and bacterial culture is purified fresh water that has been purified by reverse osmosis, distillation, deionization or other means. The culture is percolated with said purified fresh water and nutrient blend for a predetermined time forming a phyto-percolate that is biologically active in nature. The phyto-percolate is decanted from the fortified algal and bacterial culture and processed. Suitable methods of processing the phyto-percolate include filtration, centrifugation, lyophilization, purification, evaporation, concentration, dilution, and other methods. The filtering of the decanted phyto-percolate in one particular embodiment is by micro-filtration where the micro-filtration removes particles larger than about 0.22 μm.

In another aspect, this invention provides a substantially pure phyto-percolate derivative isolated from a phyto-percolate. In a preferred embodiment, the derivative is isolated from the percolate produced by culturing the microorganisms of ATCC Deposit #PTA-5863 or other appropriate species as described herein. In another embodiment, the derivative is a protein having a molecular weight of about 67.5 kDa. In related embodiments, two, three, four, five, or more phyto-percolate derivatives are produced and isolated from the culture at ATCC Deposit #PTA-5863. In a related aspect, the invention provides a composition comprising one or more phyto-percolate derivatives dissolved in an aqueous solution, wherein the solution comprises less than 150 ppm total dissolved solids.

In a related aspect, the invention provides a pharmaceutical formulation comprising a one or more (e.g., two, three, four, five, or more) substantially pure derivatives isolated from a phyto-percolate and a pharmaceutically acceptable excipient.

The term "inflammatory disorder" encompasses a variety of conditions including conditions related to a hyperactive immune system, chronic inflammation, and autoimmune disorders. Inflammatory disorders include, for example, acne vulgaris; acute febrile neutrophilic dermatosis; acute respiratory distress syndrome; Addison's disease; adrenocortical insufficiency; adrenogenital ayndrome; allergic conjunctivitis; allergic rhinitis; allergic intraocular inflammatory diseases, ANCA-associated small-vessel vasculitis; angioedema; ankylosing spondylitis; aphthous stomatitis; arthritis, asthma; atherosclerosis; atopic dermatitis; autoimmune disease; autoimmune hemolytic anemia; autoimmune hepatitis; Behcet's disease; Bell's palsy; berylliosis; balanitis circumscripta plasmacellularis; balanoposthitis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eczema (e.g., asteatotic eczema, dyshidrotic eczema, vesicular palmoplantar eczema); eosinophilic fasciitis; epicondylitis; erythema annulare centrifugum; erythema dyschromicum perstans; erythema multiforme; erythema nodosum; exfoliative dermatitis; fibromyalgia; focal glomerulosclerosis; giant cell arteritis; gout; gouty arthritis; graft-versus-host disease; granuloma annulare; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflamed prostate; inflammatory bowel or gastrointestinal disorders, inflammatory dermatoses; juvenile rheumatoid arthritis; laryngeal edema; lichen nitidus; lichen planus; lichen sclerosus et atrophicus; lichen simplex chronicus; lichen spinulosus; Loeffler's syndrome; lupus nephritis; lupus vulgaris; lymphomatous tracheobronchitis; macular edema; multiple sclerosis; musculoskeletal and connective tissue disorder; myasthenia gravis; myositis; nummular dermatitis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary billiary cirrhosis; pruritus scroti; pruritis/inflammation, psoriasis; psoriatic arthritis; Reiter's disease; relapsing polychondritis; pyoderma gangrenosum; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis.

The term "substantially pure," when referring to a phyto-percolate derivative, means the state of a substance that has been separated from the other components of the phyto-percolate. Typically, a substantially pure derivative is at least 80%, by weight, free from the proteins and other organic molecules of the phyto-percolate. Preferably, the substantially pure derivative is at least 90%, 95%, or 99%, by weight, free from those organic molecules. A substantially pure derivative may be obtained, for example, by extracting it from a source other than the phyto-percolate. To the extent that the invention calls for more than one substantially pure phyto-percolate derivative, it is understood that the combination of derivatives is substantially pure relative to the phyto-percolate.

BRIEF DESCRIPTION OF THE DRAWINGS

The foregoing and other features and advantages of the present invention will be more fully understood from the following detailed description of illustrative embodiments, taken in conjunction with the accompanying drawing in which.

DETAILED DESCRIPTION

Figure 1:
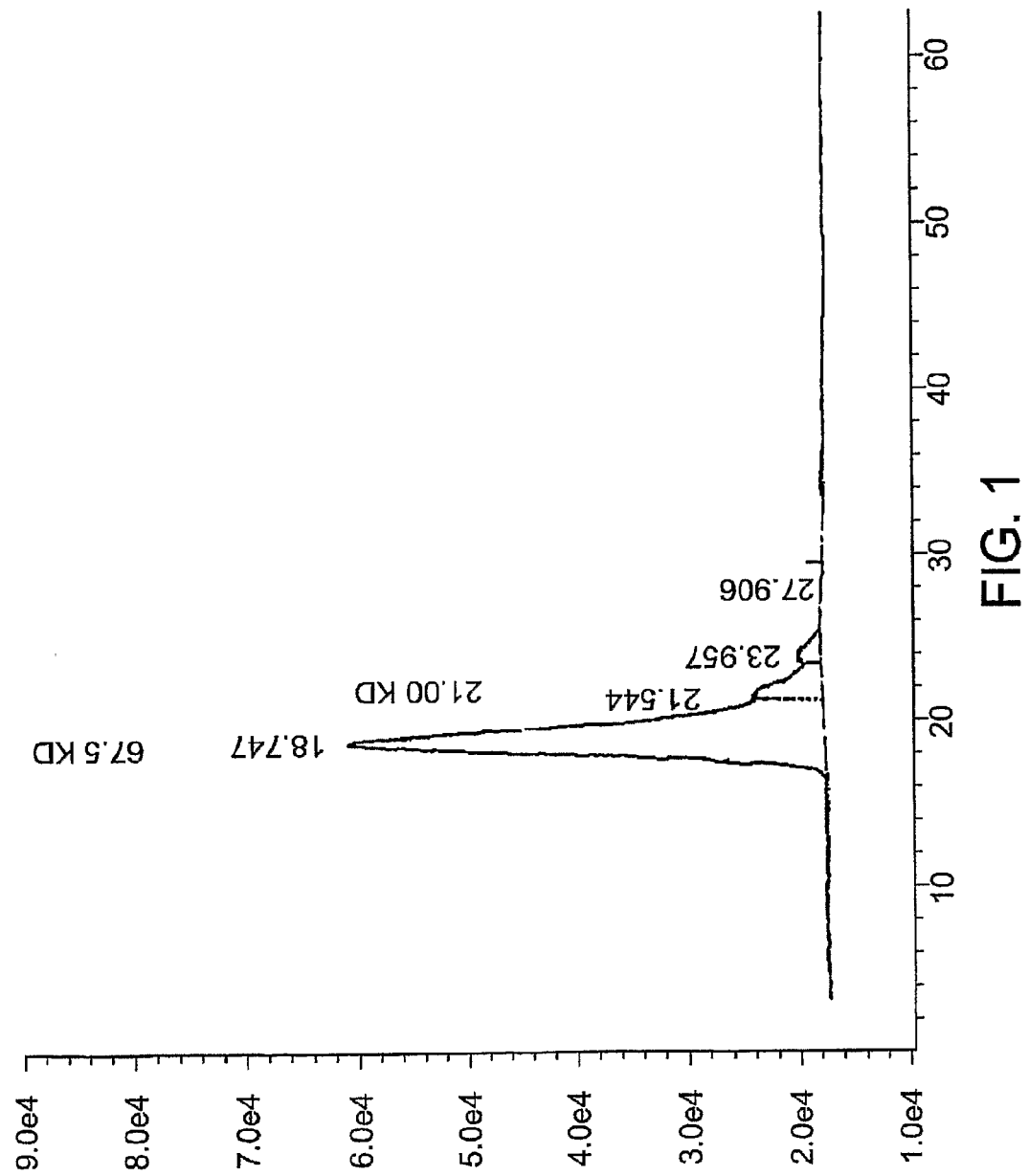
FIG. 1 is an HPLC chromatogram of the phyto-percolate.

The present invention provides a phyto-percolate that has therapeutic and other beneficial properties when administered to humans and other animals. Without being bound by any theory, it is believed that at least one of the therapeutically active agents in the phyto-percolate is enzymatic in nature. Methods for preparing the phyto-percolate are also provided. Detailed embodiments of the present invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention in virtually any appropriately detailed embodiment.

Phyto-Percolate Production

According to the invention, a phyto-percolate is derived from a culture comprised of freshwater algae, moss, bacteria, actinomycetes, and fungi. It is believed that the culture is comprised of at least one or more of the following genera:

*Acinetobacter*
*Aerococcus*
*Aeromonas*
*Aquaspirillium*
*Bacillus*
*Brevibacterium*
*Burkholderia*
*Caseobacter*
*Chlorella*
*Clavibacter*
*Corynebacterium*
*Dermacoccus*
*Liefsonia*
*Micrococcus*
*Oedocladium*
*Phyllobacterium*
*Pseudomonas*
*Ralstonia*
*Rhizobium*
*Rhodococcus*
*Riemerella*
*Roseomonas*
*Shingomonas*
*Staphylococcus*
*Stenotrophomonas*
*Stichococcus*
*Streptomyces*
*Ulothrix*
*Variovorax*
*Weeksella*
*Xanthomonas*

Particular note is made of the genera *Aquaspirillum, Bacillus, Pseudomonas, Ralstonia, Stenotrophomonas, Stichococcus, Streptomyces, Ulothrix,* and *Xanthomonas*. Without being bound by any theory, it is believed that these genera are the most abundant organisms in the culture and may be the primary producers of the therapeutically active phyto-percolate derivative(s). A deposit of a culture resulting in a phyto-percolate of the present invention has been placed in the American Type Culture Collection, of Manassas, Va., as Deposit # PTA-5863

In particular embodiments, a heterotrophic rotifer species exists in the cultures, as well as bacteria that have been identified as *Stenotrophomonas, Ralstonia, Acinetobacter, Acinetobacter, Leifsonia, Riemerella, Variovorax,* and *Streptomyces*. Without being bound to any particular theory, it is believed that these bacteria may produce enzymes or other derivatives that are contributors to the effectiveness of the phyto-percolate.

Phyto-percolate cultures of approximately 100-200 ml of dense algal cells in approximately 2.5 gal (about 10 liters), of reverse-osmosis purified water are fed liquid extract of live active yeast, or Baker's yeast, *Saccharomyces cerevisiae*, which has been prepared from 1.0 g dry active yeast added to 50 ml warm water, at between about 37° C. and about 43° C. The mixture is allowed to incubate at room temperature for 10-30 minutes, or until it slightly foams. The cultures are fed about 1 ml each, at a frequency of between every 1 to every 8 weeks It is contemplated within the scope of the invention that other yeast cultures may be used. It is further contemplated that other organic nutrients or substrates known in the art may be used such as glucose or proteose, or other algal growth media prepared from inorganic nutrients, supplements, and/or vitamins, if they support the culture's production of phyto-percolate derivatives.

In one embodiment, the cultures are grown under full-spectrum grow lights at about 25° C., and produce a final unadjusted pH of between about 6.2 to about 7 that fluctuates. The cultures are grown in clear glass fishbowl containers having a volume of approximately 2.5 gal with semi-transparent plastic lids, with the exception of about five 3 mm holes in the lid for gas exchange. Other culture containers, ingredients, conditions and methods known in the art may be used that allow the cells to grow in a manner in which the phyto-percolate derivatives are expressed. Such methods may include larger batch, semi-continuous, continuous or other type culture systems including bioreactors, photoreactors, or other fermentation technology, and may or may not include aeration or agitation, may or may not include solid, liquid, semi-solid or other form of growth media, substrate or carrier, may or may not include the above particular conditions of temperature, volume, contact time, nutrient supplementation, surface area, pH, light intensity or other environmental parameters.

In one particular embodiment, the cultures are harvested periodically by drawing off the top 1.25 gal of phyto-percolate from each 2.5 gal culture. This is referred to as the "raw phyto-percolate." The majority of the algal or other cells forming the phyto-percolate culture remain in the bottom of the culture container substantially undisturbed while the phyto-percolate is decanted. The decanted material is then processed as desired. The volume of the container is then returned to original volume with purified water at approximately room temperature (about 25° C.). Other culture and harvest systems, timetables, volumes and methods may be used for production of the phyto-percolated and its derivatives.

Without being bound by any particular theory, it is believed the patterns of harvest and feeding affect derivative production. Because microbial ecosystems are highly dynamic and are directly affected by the immediate surroundings, the food blend, such as a liquid extract of active Baker's yeast, increases the active derivative in the phyto-percolate culture compared with other foods or nutrient blends. The interaction between competing or cooperative organisms within the culture also may release, alter, or stimulate the expression of derivatives in phyto-percolate.

Methods for evaluating in vivo effects of phyto-percolate include peripheral blood observations on wet and dry blood smears, diagnostic and/or analytical blood tests, and various clinical observations and measurements such as body weight. Reductions in excess pathological fibrin and platelet aggregation have been observed, which are secondary to inflammation and tissue destruction. Increases in white blood cell mobility and number have also been observed. Anti-inflammatory effects of phyto-percolate in vivo have also been monitored with independent laboratory blood studies focusing on chronic or acute inflammatory activity and hyper-coagulant states and also with in vivo clinical animal studies evaluating the effects of phyto-percolate on rat paw edema (swelling).

Phyto-Percolate Filtration

After harvest of the phyto-percolate from the cultures, the decanted fluid is filtered through a progressive series of depth and membrane filters made of chemically-inert low-protein binding, food-safe materials. These have been shown to protect in vivo efficacy, and provide a final filtration level of about 0.22 microns, as well as being chemically inert to ozonated water. In one embodiment, for example, filters manufactured by Millipore Corporation, Catalog #'s D00501S01, CVH101TPE and CVD101TPE, constructed of polypropylene and PVDF, are suitable. Other filters know in the art may be used that are inert to the phyto-percolate derivatives and processing and sanitizing materials including, for example, ozonated water. The processing system requires sanitization to protect the integrity of phyto-percolate and its derivatives. In one embodiment, ozonated and chlorinated water are used for this purpose. Likewise, other food-safe chemical or heat sanitizers or other methods of sanitization may be used. The processing system is comprised of a series of food-safe filter housings and other plumbing and suitable mixing, bottling, transport or storage containers.

Filtration by size exclusion removes approximately >99.9% of contaminants such as bacteria, yeast and mold spores, and algal cells. It is also believed to preserve derivative activity if filter materials are made of sanitary low-protein-binding, chemically-inert materials. The resulting liquid, the phyto-percolate, is substantially comprised of water and the active derivatives. The phyto-percolate, after passing through the finishing filter is then sampled, tested and stored before and after bottling.

The phyto-percolate is processed and bottled under sanitary conditions known in the art using chemical sterilization. It is contemplated within the scope of the invention that other methods of filtration and sanitization known in the art may be used that are not unreasonably degrading of the derivative activity. The phyto-percolate is bottled and distributed or otherwise processed, until consumption. Any suitable method of processing, packing, bottling, storing, distributing and transporting known in the art may be used.

Phyto-Percolate Characterization

It is believed that the raw phyto-percolate, prior to filtration, is a complex mixture of macro- and micro-molecules. We performed several physico-chemical tests to determine the composition of the filtrate. In each case, the phyto-percolate filtrate was lyophilized, redissolved in $ddH_2O$, and refiltered to remove any undissolved particulate matter.

A sample of the lyophilized phyto-percolate was subjected to isocratic reverse phase HPLC, on a size-exclusion chromatography column (TSK-GEL Super SW Series; Tosoh Biosciences, Montgomeryville, Pa.), under non-denaturing conditions. Proteins were identified using a micro flow cell UV detector at 280 nm. As shown in FIG. 1, a major protein species of 67.5 kDa was identified (retention time 18.747 minutes). The 67.5 kDa peak contributed about 90% of the total signal measured at 280 nm. Also detected were peaks at retention times of 21.544 minutes (21.0 kDa) and 23.957 minutes. Analysis under denaturing and other conditions indicates that the 21.0 kDa species is a protein molecule and the 23.957 minute peak is primarily polysaccharide. The major components of the phyto-percolate (the 67.5 kDa protein, 21.0 kDa protein, and the polysaccharide identified at 23.957 minutes) are referred to herein as phyto-percolate derivatives and may contribute to the biological and therapeutic efficacy of the phyto-percolate.

Figure 2:
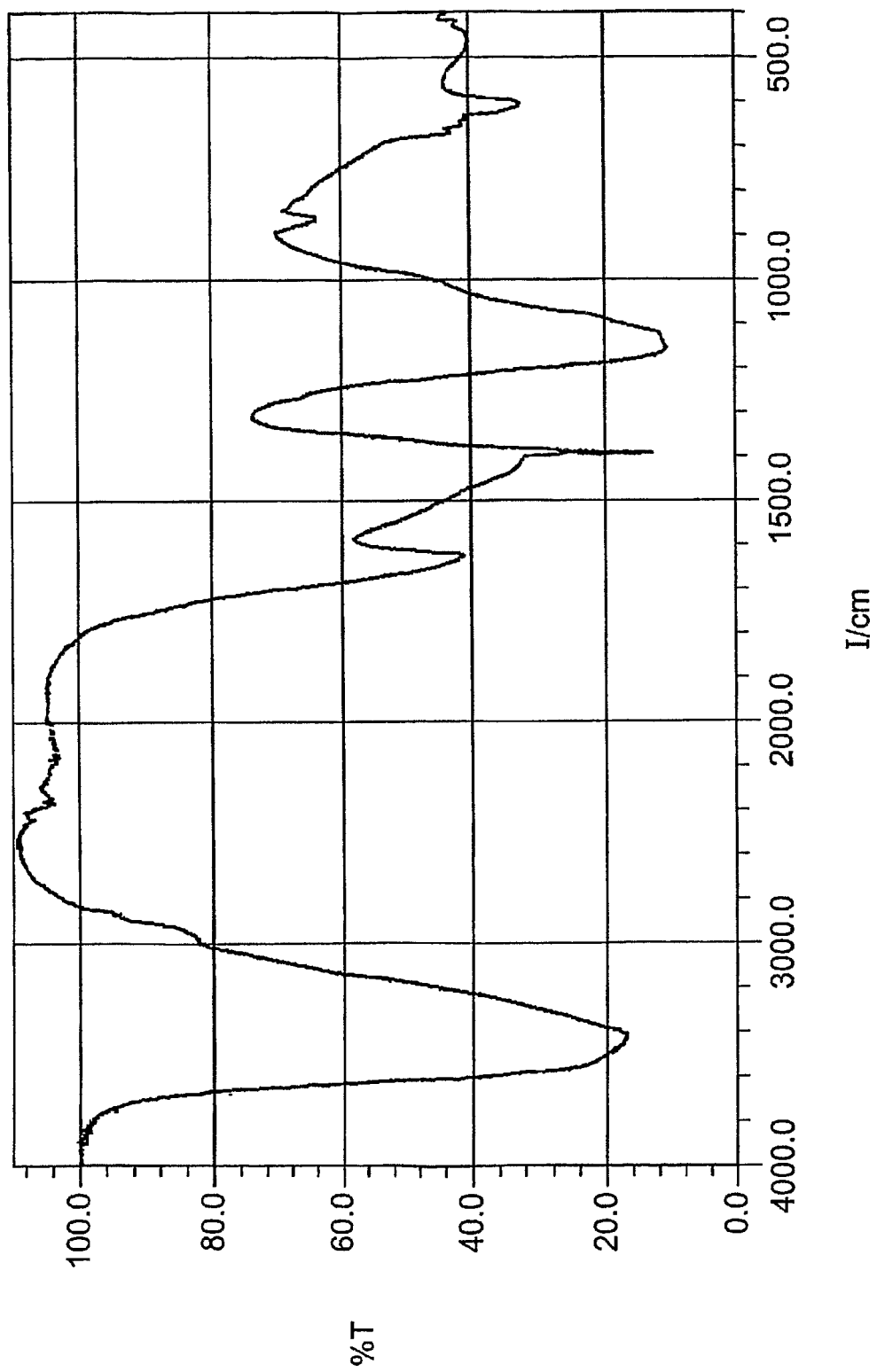
FIG. 2 is an FTIR spectrum of the phyto-percolate.

Another sample of the lyophilized phyto-percolate was subjected to Fourier Transform Infrared (FTIR) spectroscopy. The results are provided in FIG. 2. FIG. 2 shows a spectrum that is characteristic of a dissolved protein sample.

Figure 3:
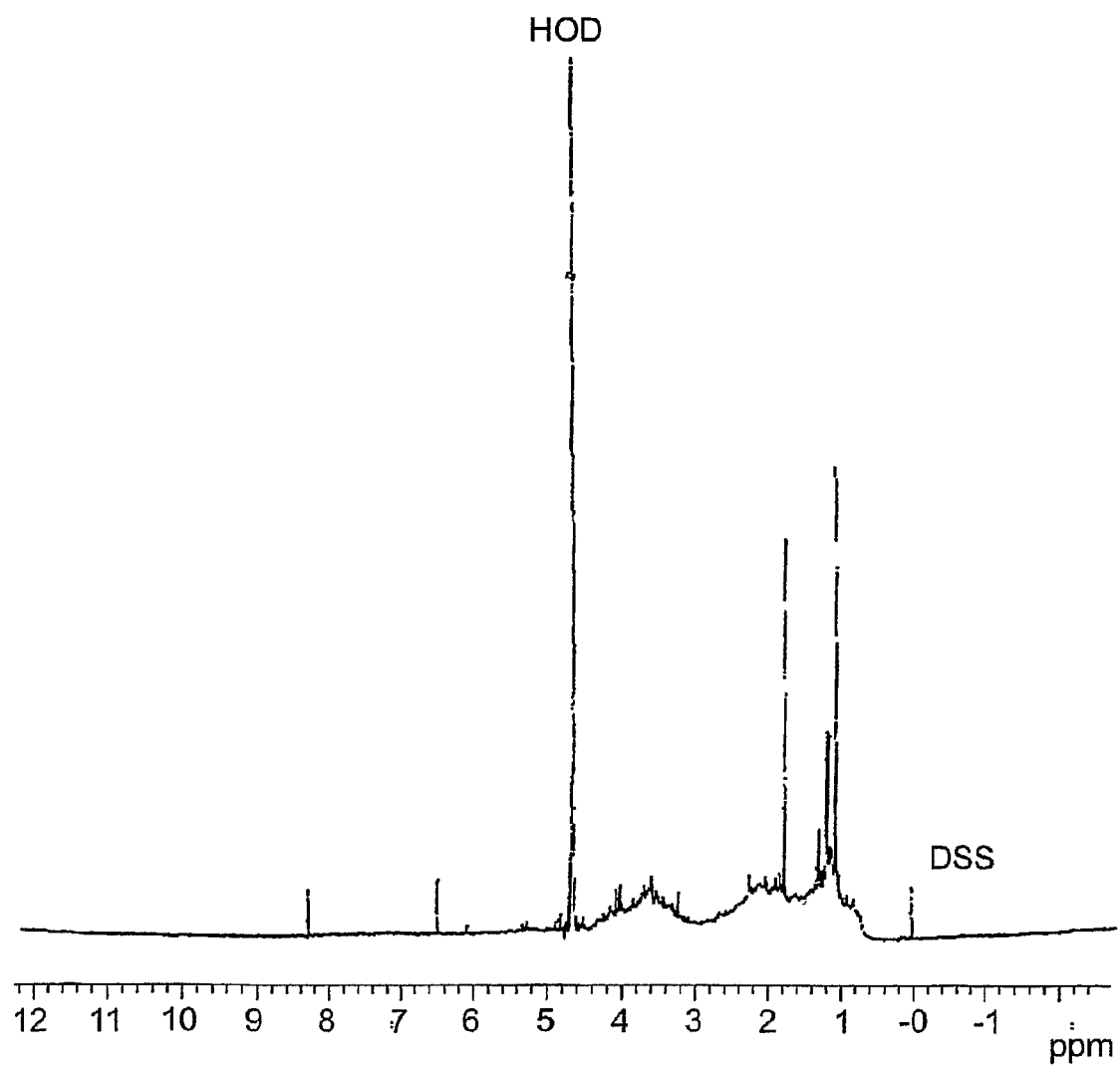
FIG. 3 is a [$^1$H]-NMR spectrum of the phyto-percolate.

A third sample of the lyophilized phyto-percolate was used for [$^1$H]-NMR. The NMR spectrum is provided in FIG. 3. Here again, the results are consistent with a single protein species.

Weight Management Using Phyto-Percolate

Excessive weight has emerged as a prominent and growing health problem. Greater than 61% of Americans over the age of 20 are overweight, 25% of whom are obese. Second only to tobacco use as the top underlying preventable cause of death, excessive weight is a major risk factor for developing diabetes, heart disease, hypertension, gallbladder disease, arthritis, cardiovascular diseases, lung diseases, and certain types of cancer.

EXAMPLE 1

Rodent Model of Weight Loss

A 21 day study using twelve mature (12 month old) Sprague-Dawley rats was performed. Each animal was orally administered 10 ml/kg of undiluted and unfiltered phyto-percolate (i.e., raw phyto-percolate) for 14 days, followed by non-dosing for 7 days. Each animal was weighted daily and observed for signs of toxicity. As shown in more detail in Table 1, the rats lost an average of 33 grams (6.3%) of body weight over the initial 14 day dosing period. They immediately began to regain lost body weight upon cessation of phyto-percolate administration. By the 21 day time point (7 days of non-dosing), the rats had lost an average of 25 grams (4.7%) of initial body weight (i.e., gained an average of 8 grams since phyto-percolate cessation).

The test animals were observed for adverse reactions immediately after each dose and at 4 and 24 hours subsequent. Daily observation for adverse reactions was continued during the 7 day non-dosing period. Specifically, clinical observations for adverse reactions were made for respiration, motor activity, convulsions, reflexes, ocular signs, salivation, piloerection, analgesia, muscle tone, gastrointestinal effects, and skin/dermal alterations. Gastrointestinal effects were the only observed adverse reaction. Soft to loose stool was observed in all test animals. No other adverse reaction was observed.

TABLE 1

Individual Weight Loss Data

| Test Subject | Pre-dosing Weight (g) | 14 Day Weight (g) | Weight Loss (% Initial Body Weight) | 21 Day Weight (g) | Weight Loss (% Initial Body Weight) |
| --- | --- | --- | --- | --- | --- |
| 1 | 484 | 443 | 41 (8.5%) | 453 | 31 (6.4%) |
| 2 | 482 | 461 | 21 (4.4%) | 479 | 3 (0.6%) |
| 3 | 549 | 521 | 28 (5.1%) | 531 | 18 (3.3%) |
| 4 | 536 | 499 | 37 (6.9%) | 507 | 29 (5.4%) |
| 5 | 510 | 462 | 48 (9.4%) | 468 | 42 (8.2%) |
| 6 | 488 | 459 | 29 (5.9%) | 465 | 23 (4.7%) |
| 7 | 535 | 506 | 29 (5.4%) | 514 | 21 (3.9%) |
| 8 | 586 | 558 | 28 (4.8%) | 562 | 24 (4.1%) |
| 9 | 569 | 504 | 65 (11.4%) | 518 | 51 (9.0%) |
| 10 | 522 | 492 | 30 (5.7%) | 498 | 24 (4.6%) |
| 11 | 556 | 532 | 24 (4.3%) | 537 | 19 (3.4%) |
| 12 | 524 | 503 | 21 (4.0%) | 507 | 17 (3.2%) |
| AVG | 528.4 | 495.0 | 33.4 (6.3%) | 503.3 | 25.1 (4.7%) |

EXAMPLE 2

Human Weight Loss and Glucose Control Study

A single-center, prospective, randomized, triple-masked, placebo-controlled parallel-group-design pilot clinical trial of the phyto-percolate was performed using two different batches of the phyto-percolate. This trial was conducted in accordance with FDA regulations and under a protocol approved by an Institutional Review Board (IRB).

Subjects: Primary inclusion criteria were men and women having a body mass index (BMI) of 25-40 m/kg$^2$, 18-70 years old (inclusive), and desirous of losing weight. Major exclusion criteria were moderate to severe co-morbid disease (e.g., cancer); history of stroke, transient ischemic attack (TIA), or similar conditions; uncontrolled hypertension, insulin-dependent diabetes, renal disease, moderately severe cardiac disease, lupus, alcohol abuse, and current or recent use of certain medications including medications and/or supplements for weight loss, glucose management, or arthritis. Women were excluded if they were pregnant, nursing, or actively trying to become pregnant.

Protocol: Patients were assigned to self-administer one ounce of filtered phyto-percolate or placebo three times each day (t.i.d.) on an empty stomach at least 30 minutes before a meal. Subjects were asked to participate in a reduced carbohydrate diet and light exercise program and complete a one-day-per-week Food Log and a daily Exercise Log for the duration of the clinical trial. Patients were evaluated during a baseline examination and then again at 2-week, 4-week, and 6-week visits. Evaluations included measurement of body weight, arm and waist circumference, and body fat measurements.

Glucose Control Study: At the baseline examination and at the 4-week and 6-week visits, patients' fasting (12 hour) blood glucose was measured and then their blood glucose was measured one hour after a glucose challenge (25 grams of jelly beans; 90.4% carbohydrate). The difference between the glucose challenge reading and the baseline reading in a single visit is an indicator of the patient's ability to regulate serum glucose levels.

Test Materials: The patients in the treatment groups were assigned one of two different lots (Batch 1 and Batch 2) of phyto-percolate prepared as described above. The placebo product was similar in appearance (color, viscosity, and odor) to the phyto-percolate. All test materials were dispensed in unlabeled blue bottles with instructions to refrigerate after opening.

Enrollment: A total of 44 subjects were enrolled and randomized for this trial. Ten subjects completed the study on Batch 1 (Cohort 1) of the phyto-percolate and twelve subjects completed Batch 2 (Cohort 2). Seven subjects completed the placebo phase of the trial.

Results: There were no significant adverse events reported. Patients in the treatment arms of the study reported greater energy and reduced hunger compared to the Placebo group. The remaining results are as follows:

After 2, 4, and 6 weeks of treatment with the filtered phyto-percolate, the average percent total weight loss (above placebo) for all treated patients (Cohorts 1 and 2; n=22) 77.7%, 48.5%, and 68.1%, respectively. After six weeks of phyto-percolate treatment, Cohort 1 lost an average of 106% (9.03 lbs) and Cohort 2 lost an average of 37% (6.01 lbs) more than the weight loss measured in the Placebo group (4.39 lbs).

TABLE 2

| | Average Weight Loss | | |
|---|---|---|---|
| | 2-Week | 4-Week | 6-Week |
| Placebo (n = 7) | 2.60 | 3.71 | 4.39 |
| Cohort 1 (n = 10) | 5.71 | 6.81 | 9.03* |
| Cohort 2 (n = 12) | 3.71 | 4.43 | 6.01 |

$p < 0.10$ (unpaired Student's t-test)

TABLE 3

Frequency Distribution of Weight Loss in Individual Patients at 6 Weeks

| Weight Change | Placebo (number of patients) | Cohort 1 (number of patients) |
|---|---|---|
| >+1 lb. | — | 1 |
| +1 lb. to −1 lb. | — | 1 |
| −1 lb. to −3 lb. | 2 | — |
| −3 lb. to −5 lb. | 2 | — |
| −5 lb. to −7 lb. | 3 | 1 |
| −7 lb. to −9 lb. | — | 3 |
| −9 lb. to −11 lb. | — | 2 |
| −11 lb. to −13 lb. | — | — |
| −13 lb. to −15 lb. | — | — |
| −15 lb. to −17 lb. | — | 1 |
| −17 lb. to −19 lb. | — | — |
| >−19 lb. | — | 1* |

*maximum weight loss was 28 lbs.

TABLE 4

Arm and Waist Circumference - Difference Between Baseline and 6 Weeks

| | Placebo | Cohort 1 | Cohort 2 |
|---|---|---|---|
| Arm | 0.083" | 0.41"* | 0.13" |
| Waist | 1.09" | 2.08"** | 1.34" |

*$p < 0.042$
**$p < 0.21$

TABLE 5

Body Composition - Percent Body Fat: Difference Between Baseline and 6 Weeks

| | Placebo | Cohort 1 | Cohort 2 |
|---|---|---|---|
| Body Fat @ Baseline | 39.1% | 39.2% | 39.0% |
| Improvement in Body Fat (lbs) | 2.11 | 6.03* | 2.89 |
| Improvement in Lean Mass (lbs) | 0.16 | 0.79** | 0.24 |

*$p < 0.01$
**$p < 0.15$

TABLE 6

Frequency Distribution of Body Fat Loss in Individual Patients at 6 Weeks

| Weight Change | Placebo (number of patients) | Cohort 1 (number of patients) |
|---|---|---|
| >+1 lb. | — | 2 |
| +1 lb. to −1 lb. | 2 | 1 |
| −1 lb. to −3 lb. | 2 | — |
| −3 lb. to −5 lb. | 2 | 2 |
| −5 lb. to −7 lb. | 1 | 2 |
| −7 lb. to −9 lb. | — | — |
| −9 lb. to −11 lb. | — | 1 |
| −11 lb. to −13 lb. | — | — |

TABLE 6-continued

Frequency Distribution of Body Fat Loss in Individual Patients at 6 Weeks

| Weight Change | Placebo (number of patients) | Cohort 1 (number of patients) |
|---|---|---|
| −13 lb. to −15 lb. | — | — |
| −15 lb. to −17 lb. | — | 1 |
| −17 lb. to −19 lb. | — | — |
| >−19 lb. | — | 1 | maximum weight loss was 28 lbs.

TABLE 7

Serum Glucose Levels In Individual Patients In Cohort 1 (mg/dl)

| | Baseline | | | 4-Week | | | 6-Week | | |
|---|---|---|---|---|---|---|---|---|---|
| Patient | Fast | Chal. | Diff. | Fast | Chal. | Diff. | Fast | Chal. | Diff. |
| 1 | 158 | 264 | 106 | 155 | 246 | 91 | 152 | 238 | 86 |
| 2 | 72 | 128 | 56 | 89 | 107 | 18 | 80 | 94 | 14 |
| 3 | 75 | 135 | 60 | 87 | 130 | 43 | 91 | 117 | 26 |
| 4 | 73 | 128 | 55 | 78 | 74 | −4 | 76 | 80 | 4 |
| 5 | 105 | 151 | 46 | 104 | 127 | 23 | 103 | 125 | 22 |
| 6 | 139 | 210 | 71 | 129 | 198 | 69 | 126 | 181 | 55 |
| 7 | 145 | 204 | 59 | 124 | 200 | 76 | 132 | 195 | 63 |
| 8 | 85 | 122 | 37 | 74 | 159 | 85 | 83 | 133 | 50 |
| 9 | 91 | 143 | 52 | 91 | 125 | 34 | 92 | 121 | 29 |
| 10 | 78 | 119 | 41 | 92 | 99 | 7 | 88 | 98 | 10 |
| Mean | | | 58.3 | | | 44.2 | | | 35.9 |
| n > 126* | 3 | | | 2 | | | 2 | | |

*values >126 mg/dl are indicative of diabetes.

TABLE 8

Group Mean Data For Glucose Tolerance Test (mg/dl)

| | Baseline | 4-Week | 6-Week |
|---|---|---|---|
| Placebo | 61.7 | 58.3 | 54.0 |
| Improvement | | 3.4 (5.5%) | 7.7 (12.3%) |
| Cohort 1 | 58.3 | 44.2 | 35.9 |
| Improvement | | 14.1 (24.2%) | 22.4 (39.6%)* |
| Cohort 2 | 60.6 | 56.2 | 55.4 |
| Improvement | | 4.2 (6.9%) | 5.2 (8.6%) |

*p < 0.08

Conclusions: The weight loss, improvement in body fat, improvement in glucose control, as well as energy and hunger categories over the course of this six-week study for those on the phyto-percolate was strong, particularly when compared to the placebo group. Cohort 1 lost about twice as much weight (1.5 lbs/week) as the placebo group (0.78 lbs/week). Seven of the ten subjects in Cohort 1 lost seven pounds or more, while none of the seven in the placebo group lost that much weight. Correspondingly, a significant reduction in waist size was measured in Cohort 1.

Significant improvements also were measured in the glucose tolerance test. Test subjects demonstrated an average of 2.6×(156%) and 1.7×(69%) improved glucose control at 4 weeks and 6 weeks, respectively, when compared to the placebo group. Furthermore, 6 of the 22 test subjects met the clinically important criterion of >50% control over baseline. Three of these six demonstrated complete control of the glucose challenge, defined as >85% glucose control over baseline.

In Vitro Anti-inflammatory Effects: COX-2 Inhibition

Cyclooxygenase-2 (COX-2) is a key regulator of the inflammatory cascade. COX-2 inhibitors are believed to reduce-inflammation by blocking prostaglandin production. In view of the adverse effects associated with mixed COX inhibitors (aspirin, ibuprofen, and naproxen) and the presently available COX-2-specific inhibitors (valdecoxib, celecoxib, rofecoxib), there is a need for improved anti-inflammatory therapies with fewer side effects.

Five concentrations of the phyto-percolate were screened, using an in vitro assay, for COX-2 inhibition. Riendeau et al., Can. J. Physiol. Pharmacol. 75: 1088-1095, 1997; Warner et al., Proc. Natl. Acad. Sci. USA 96: 7563-7568, 1999. Briefly, this assay measured the conversion of 0.3 µM arachidonic acid to $PGE_2$ by human recombinant insect Sf21 cells expression human COX-2. The incubation buffer contained 100 mM Tris-HCl (pH 7.7), 1 mM glutathione, 1 µM hematin, and 500 µM phenol. $PGE_2$ was quantified using an enzyme-linked immunoassay (EIA).

Sample 1 was a lyophilized sample of phyto-percolate that was reconstituted just prior to assay in a final assay volume of 100 µl. Rofecoxib was used as a positive control for COX-2 inhibition. The sample was assayed in five concentrations in duplicate and compared to reference standard.

TABLE 9

COX-2 Inhibition By Phyto-percolate

| Sample | Concentration | % COX-2 Inhibition (average of duplicates) | $IC_{50}$ |
|---|---|---|---|
| 1 | 10 mg/ml | 99 | 141 µg/ml |
| | 3 mg/ml | 101 | |
| | 1000 µg/ml | 97 | |
| | 300 µg/ml | 68 | |
| | 100 µg/ml | 41 | |

The $IC_{50}$ value for Sample 1 was calculated using the assumption that the 67.5 kDa protein species is the active compound, resulting in an IC50 value of 1.54 µM.
An IC50 value for reference compound Rofecoxib, Batch 146358 was 0.0869 µM.

In Vitro Anti-Inflammatory Effects: LIPOX-15 & -5 Inhibition

Lipoxygenases (15-LO & 5-LO) are key regulators of the inflammatory cascade. LIPOX inhibitors are believed to reduce inflammation by blocking leukotriene production. LIPOX inhibitors may be used instead of, or in conjunction with COX inhibitors to provide anti-inflammatory therapy.

One concentration of the phyto-percolate was screened, using in vitro assays, for 15-LO and 5-LO inhibition. Samples 2 & 3 are identical aliquots of Sample 1 used in the COX-2 inhibition assay. These samples were lyophilized aliquotes of phyto-percolate that were reconstituted just prior to assay in a final assay volume of 100 µl. PD-146176 was used as a positive control for 15-LO inhibition and NDGA was used as a positive control for 5-LO inhibition. The sample was assayed in one concentration in duplicate and compared to reference standards.

Briefly, the 15-LO assay measures the conversion of 256 µM linoleic acid to 13-HPODE. The assay is incubated in phosphate-buffered saline buffer, pH 7.4 at 4° C. 13-HPODE was spectrophotometrically quantified and compared to reference compound PD-146176. Carter G W et al. J Pharmacol Exp Ther. 256(3):929, 1991; Safayhi H et al. Planta Medica. 66:110, 2000.

Briefly, the 5-LO assay measures the conversion of arachidonic acid to LTB4, expressed by human PBML cells. The reaction was incubated in Hank's Balanced Salt Solution at 37° C. LTB4 was spectrophotometrically quantified and compared to reference compound NDGA. Auerbach B J et al. Anal Biochem. 201:375, 1992.

TABLE 10

15-LO Inhibition By Phyto-percolate

| Sample | Concentration | % 15-LO Inhibition (average of duplicates) |
|---|---|---|
| 2 | 10 mg/ml | 107 |

TABLE 11

5-LO Inhibition By Phyto-percolate

| Sample | Concentration | % 5-LO Inhibition (average of duplicates) |
|---|---|---|
| 3 | 10 mg/ml | 99 |

In Vivo Anti-Inflammatory Effects: Carageenan-Induced Paw Edema

The carrageenan-induced paw edema assay was used as an in vivo indicator of the anti-inflammatory effects of the phyto-percolate. Carrageenan induces local inflammation and edema when injected into the paw pad of a rat (Di Rosa et al., 1971). The development of paw edema is believed to be biphasic (Vinegar et al., 1969). The initial phase is attributable to the local release of histamine and serotonin (Crunkhon et al., 1971) and the second phase is caused by prostaglandin release as a result of COX activation. The second phase is measured as an increase in paw volume and has been demonstrated to be responsive to steroidal and non-steroidal anti-inflammatory agents.

Groups of test subjects (n=6) received oral doses of either vehicle control (water; 5 ml/kg), indomethacin (30 mg/kg), aspirin (100 mg/kg), unfiltered phyto-percolate (10 ml/kg), or filtered phyto-percolate (10 ml/kg) 30 minutes prior to intraplantar administration of carrageenan (0.1 ml of a 1% solution). Paw volume was measured at 0, 2, 4, 6, 8, and 20 hours after treatment using a plethysmometer to measure volume displacement. Each treatment group is compared to control.

As shown in Table 12, the paw volume of the control animals and all treatment groups nearly doubled in two hours and remained so through the four hour time point. By six hours, paw volume was reduced by 30% and 50% in the groups administered the filtered and unfiltered phyto-percolate, respectively. This reduction in edema was significantly better than that observed for either the indomethacin or the aspirin groups at this time. Further, the reduction in edema measured for the two phyto-percolate groups was comparable to both the indomethacin and aspirin groups at the 8 hour and 20 hour time points.

TABLE 12

In Vivo Anti-inflammatory Effects of Phyto-percolate
Mean paw volume (ml) ± SD (% change from control)

| Group | 0 hours | 2 hours | 4 hours | 6 hours | 8 hours | 20 hours |
|---|---|---|---|---|---|---|
| Control | 1.24 ± 0.17 | 2.18 ± 0.24 | 2.17 ± 0.27 | 2.12 ± 0.15 | 2.05 ± 0.08 | 1.85 ± 0.08 |
| Indomethacin | 1.25 ± 0.05 (1%) | 2.25 ± 0.23 (7%) | 2.18 ± 0.22 (1%) | 2.00 ± 0.22 (−12%) | 1.83 ± 0.23 (−22%) | 1.37 ± 0.10 (−38%) |
| Aspirin | 1.25 ± 0.08 (1%) | 2.22 ± 0.28 (4%) | 2.07 ± 0.23 (−10%) | 1.92 ± 0.18 (−20%) | 1.80 ± 0.18 (−25%) | 1.42 ± 0.16 (−23%) |
| Filtered | 1.22 ± 0.04 (−2%) | 2.15 ± 0.10 (−3%) | 2.15 ± 0.10 (−2%) | 1.78 ± 0.10 (−34%) | 1.78 ± 0.10 (−27%) | 1.35 ± 0.08 (−30%) |
| Unfiltered | 1.20 ± 0.13 (−4%) | 2.15 ± 0.12 (−3%) | 2.13 ± 0.10 (−4%) | 1.67 ± 0.10 (−45%) | 1.67 ± 0.10 (−38%) | 1.28 ± 0.12 (−37%) |

Immunological Effects: Rodent Model of HIV Infection

The effect of treatment using the phyto-percolate was investigated using a rat model of HIV infection. The HIV model used inoculates rats with seven (7) of the nine (9) HIV genes, making it a non-contagious model that develops full symptoms of HIV by 9 months after inoculation, with a life expectancy of 12 months.

Some of the most devastating symptoms of HIV manifest themselves in the liver and the immune system. Liver problems are frequent causes of illness and death in people with HIV infection. Throughout the study, liver function tests including AST, ALT, GGTP, bilirubin, and albumin were monitored in the treatment and control groups. C-reactive protein was assayed as an inflammatory marker. The immune response was monitored using IgG, IgA, and IgM levels which are known to decline during the progression of AIDS.

For testing, serum was drawn by cardiac puncture for baseline (pre-inoculation) values. The treatment group received phyto-percolate for their drinking water, which was allowed ad libitum, while the control group received filtered water. Serum was drawn by cardiac puncture, as above, every thirty (30) days until the termination of the study.

After 60 days of treatment with the phyto-percolate, the treatment group had an average 30% increase in IgA levels, 50% increase in IgG levels, and a 40% reduction in C-reactive protein (C-RP) levels, relative to the untreated group (Table 13). No significant differences in body weight, average daily food consumption, or average daily liquid consumption were detected between the groups.

TABLE 13

Serum Analysis From Rat HIV Study

| Animal Group | AST (U/L) | ALT (U/L) | Bilirubin (mg/dL) | C-RP (mg/ml) | IgG (mg/dL) | IgM (mg/dL) | IgA (mg/dL) |
|---|---|---|---|---|---|---|---|
| Control | | | | | | | |
| Base | 117 | 70 | 0.07 | 3.41 | 57 | 27 | 18 |
| 1 Mo. | 95 | 60 | 0.12 | 0.65 | 69 | 26 | 24 |
| 2 Mo. | 122 | 67 | 0.12 | 0.93 | 120 | 26 | 24 |
| HIV | | | | | | | |
| Base | 116 | 77 | 0.07 | 3.37 | 60 | 26 | 21 |
| 1 Mo. | 166 | 76 | 0.21 | 0.58 | 108 | 27 | 25 |
| 2 Mo. | 139 | 81 | 0.13 | 0.56 | 167 | 23 | 38 |

Administration of Phyto-Percolate

The phyto-percolate dosage will vary with the nature and severity of the disease, the biochemical activity of the disease, and the age and weight of the subject. The effects of using the phyto-percolate will be measured using standard parameters known in the art for any such disease state. As described in several of the foregoing examples, one derivative, the 67.5 kDa species, is normally present in the phyto-percolate at about 10 ppm to about 150 ppm as measured by HPLC and UV detection (described above). Depending upon the severity of disease or desired clinical outcome, the concentration of phyto-percolate may be altered. For example, a large sample of the phyto-percolate may be partially dried in order to concentrate the therapeutically active derivatives so that they may be administered in a more convenient liquid dosage size.

It is also contemplated that the solid fraction is isolated from the phyto-percolate (e.g., by complete drying) and formulated for oral or parenteral administration (e.g., intravenous, intramuscular, and subcutaneous injection, topical, rectal or vaginal administration or other). Methods well known in the art for making formulations are found, for example, in Remington: The Science and Practice of Pharmacy (21st edition), ed. R. Hendrickson, 2005, Lippincott Williams & Wilkins, Baltimore, Md. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated napthalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds.

In an adult subject, an oral dosage of the phyto-percolate or derivative is typically administered on an empty stomach. Dosing on an empty stomach is most desirable because of the potential for interference on phyto-percolate absorption or function. For example, the active phyto-percolate derivatives may be inhibited by food-stimulated gastrointestinal activities, by adsorption of phyto-percolate derivatives to food particles, or by pharmacological inhibition by food components (e.g., ions or inhibitory macromolecules).

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Other embodiments are within the claims.

What is claimed is:

1. A method of treating inflammation or managing weight in a mammal, said method comprising administering to said mammal a therapeutically effective amount of phyto-percolate derived from culturing microorganisms of ATCC Deposit #PTA-5863.

2. The method of claim 1, wherein said phyto-percolate has fibrinolytic activity.

3. The method of claim 1, wherein said therapeutically effective amount is between about 1 ounce to about 20 ounces per day of said phyto-percolate.

4. The method of claim 1, wherein said inflammation is an inflammatory disorder selected from the group comprised of arthritis, rheumatoid arthritis, ulcerative colitis, and inflammatory bowel disease.

5. The method of claim 1, wherein said mammal is selected from the group consisting of a human, a dog, a cat, a horse, and a cow.

6. The method of claim 1, wherein said compound functions as a broad spectrum anti-inflammatory agent.

7. The method of claim 1 wherein said inflammation is acute inflammation.

8. The method of claim 1 wherein said inflammation is chronic inflammation.

9. The method of claim 7 wherein said acute inflammation is generalized.

10. The method of claim 7 wherein said acute inflammation is specifically located.

11. The method of claim 8 wherein said chronic inflammation is generalized.

12. The method of claim 8 wherein said chronic inflammation is specifically located.

13. The method of claim 1 wherein said mammal is a pig.

14. The method of claim 1 wherein said mammal is a hog.

* * * * *